(12) United States Patent
Kelly et al.

(10) Patent No.: US 11,553,854 B2
(45) Date of Patent: Jan. 17, 2023

(54) MEDICAL DEVICE WITH GUIDEWIRE DETECTION

(71) Applicant: Lake Region Manufacturing, Inc., Chaska, MN (US)

(72) Inventors: Sean Kelly, Galway (IE); John Michael Hayes, Cork (IE)

(73) Assignee: Lake Region Manufacturing, Inc., Chaska, MN (US)

( * ) Notice: Subject to any disclaimer, the term of this patent is extended or adjusted under 35 U.S.C. 154(b) by 1038 days.

(21) Appl. No.: 16/248,937

(22) Filed: Jan. 16, 2019

(65) Prior Publication Data

US 2019/0224451 A1     Jul. 25, 2019

Related U.S. Application Data

(60) Provisional application No. 62/619,406, filed on Jan. 19, 2018.

(51) Int. Cl.
| | |
|---|---|
| *A61B 5/06* | (2006.01) |
| *A61M 25/09* | (2006.01) |
| *A61B 5/00* | (2006.01) |
| *A61M 25/01* | (2006.01) |

(52) U.S. Cl.
CPC .............. *A61B 5/06* (2013.01); *A61B 5/062* (2013.01); *A61B 5/063* (2013.01); *A61B 5/6851* (2013.01); *A61M 25/09* (2013.01); *A61M 25/09041* (2013.01); *A61M 2025/0166* (2013.01); *A61M 2205/18* (2013.01); *A61M 2205/3317* (2013.01); *A61M 2205/583* (2013.01)

(58) Field of Classification Search
CPC .......... A61B 5/062; A61B 5/063; A61B 5/06; A61B 5/061; A61B 5/6851; A61M 2205/3317; A61M 2025/0166; A61M 25/09041; A61M 5/46; A61M 25/0606
See application file for complete search history.

(56) References Cited

U.S. PATENT DOCUMENTS

| | | |
|---|---|---|
| 5,425,367 A | 6/1995 | Shapiro et al. |
| 6,309,370 B1 * | 10/2001 | Haim ................ A61M 25/0082 607/122 |
| 7,158,754 B2 | 1/2007 | Anderson |

(Continued)

FOREIGN PATENT DOCUMENTS

| | | | |
|---|---|---|---|
| EP | 3000497 A2 * | 3/2016 | ......... A61B 17/3403 |
| WO | WO-0048512 A1 * | 8/2000 | ............ A61B 5/055 |
| WO | 2018042271 | 3/2018 | |

*Primary Examiner* — Theodore J Stigell
*Assistant Examiner* — Rachel T. Smith
(74) *Attorney, Agent, or Firm* — Michael P. Horvath (57) ABSTRACT

In various examples, a medical device is configured to be at least partially insertable within a patient. The medical device includes a first elongate member including a sidewall surrounding and defining a lumen extending through the first elongate member between a first proximal end and a first distal end. A second elongate member is sized and shaped to fit within the lumen of the first elongate member. A coil is disposed within the sidewall of the first elongate member, wherein the coil is configured to sense a position of the second elongate member with respect to the coil. In some examples, the first elongate member includes a catheter, and the second elongate member includes a guidewire.

22 Claims, 5 Drawing Sheets

(56) References Cited

U.S. PATENT DOCUMENTS

| | | | |
|---|---|---|---|
| 7,881,769 B2* | 2/2011 | Sobe | A61B 34/20 |
| | | | 600/424 |
| 9,211,094 B2 | 12/2015 | Ludwin et al. | |
| 9,283,334 B2* | 3/2016 | Mantell | G01F 1/56 |
| 2008/0140006 A1* | 6/2008 | Eskuri | A61B 5/6848 |
| | | | 604/117 |
| 2009/0062739 A1 | 3/2009 | Anderson | |
| 2016/0007880 A1 | 1/2016 | Duindam | |
| 2016/0235337 A1 | 8/2016 | Govari et al. | |
| 2018/0169389 A1 | 6/2018 | Lemon et al. | |

\* cited by examiner

MEDICAL DEVICE WITH GUIDEWIRE DETECTION

CROSS REFERENCE TO RELATED APPLICATIONS

This application claims the benefit of priority to U.S. Provisional Application Ser. No. 62/619,406, filed on Jan. 19, 2018, entitled "CATHETER FOR DETECTING WIRE AT DISTAL TIP," which is incorporated by reference herein in its entirety.

BACKGROUND

When a medical device, such as, for instance, a catheter, is at least partially inserted within a patient, it is challenging to know if or when another medical device, such as, for instance, a guidewire, is at or extending from a distal end of the catheter. Some current methods of determining if a guidewire is located at the distal end of a catheter include using x-ray or fluoroscopy or using depth markers on the guidewire and aligning them with a proximal end of the catheter.

However, each of these methods can be problematic. For instance, using x-ray or fluoroscopy exposes the patient to radiation, which could result in radiation-induced injuries or diseases to the patient. Moreover, using x-ray or fluoroscopy requires a radiopaque marker on the guidewire, which can increase the cost and complexity of the guidewire necessary for the procedure. Using depth markers requires a specifically-marked guidewire to be matched to the catheter being used (for instance, only a 100-cm marker on the guidewire will work with a 100-cm catheter). Additionally, depth markers only give an indication that the guidewire may be at the distal tip of the catheter. Depth markers cannot guarantee that the guidewire is at the distal tip of the catheter.

OVERVIEW

This overview is intended to provide an overview of subject matter of the present patent document. It is not intended to provide an exclusive or exhaustive explanation of the invention. The detailed description is included to provide further information about the present patent document.

The present inventors have recognized, among other things, that the present subject matter can be used to detect a guidewire at or extending from a distal end of a catheter without exposing a patient to unnecessary radiation and without the need for a marker band on a guidewire. Also, the present subject matter is advantageous in that it allows one to know if a guidewire is extending from a distal end of a catheter without the need for specifically matched guidewires and catheters. In various examples, the present subject matter is advantageous in that it provides a way to detect a position of the guidewire with respect to the catheter regardless of guidewire length or catheter length. To better illustrate the devices described herein, a non-limiting list of examples is provided here:

Example 1 can include subject matter that can include a medical device configured to be at least partially insertable within a patient. The medical device includes a first elongate member including a first proximal end, a first distal end, and a sidewall surrounding and defining a lumen extending through the first elongate member between the first proximal end and the first distal end. A second elongate member includes a second proximal end and a second distal end. The second elongate member is sized and shaped to fit within the lumen of the first elongate member. A coil is disposed within the sidewall of the first elongate member, wherein the coil is configured to sense a position of the second elongate member with respect to the coil.

In Example 2, the subject matter of Example 1 is optionally configured such that the coil is disposed proximate the first distal end of the first elongate member to sense the second elongate member in proximity to the first distal end of the first elongate member.

In Example 3, the subject matter of Example 1 or 2 is optionally configured such that the coil is disposed within the sidewall around the lumen of the first elongate member.

In Example 4, the subject matter of any one of Examples 1-3 is optionally configured such that, with the second elongate member in a first position spaced from the coil, the coil includes a first inductance, and, with the second elongate member in a second position proximate the coil, the coil includes a second inductance different from the first inductance.

In Example 5, the subject matter of any one of Examples 1-4 optionally includes a sensor circuit including the coil and a capacitor.

In Example 6, the subject matter of any one of Examples 1-5 optionally includes a control unit electrically coupled to the coil. The control unit is configured to determine a position of the second elongate member with respect to the coil based upon an inductance of the coil.

In Example 7, the subject matter of Example 6 is optionally configured such that the control unit includes an output module configured to indicate the position of the second elongate member with respect to the coil.

In Example 8, the subject matter of Example 7 is optionally configured such that the output module includes a light that lights up or an alarm that sounds to indicate the position of the second elongate member with respect to the coil.

In Example 9, the subject matter of Example 7 or 8 is optionally configured such that the output module includes a display screen to indicate the position of the second elongate member with respect to the coil.

In Example 10, the subject matter of any one of Examples 6-9 optionally includes a receptacle configured to accept the proximal end of the first elongate member and electrically couple the coil to the control unit.

In Example 11, the subject matter of Example 10 is optionally configured such that the first elongate member includes an opening in the sidewall to allow access to the lumen of the first elongate member with the proximal end of the first elongate member disposed within the receptacle.

In Example 12, the subject matter of any one of Examples 1-11 is optionally configured such that the first elongate member includes a catheter.

In Example 13, the subject matter of any one of Examples 1-12 is optionally configured such that the second elongate member includes a guidewire.

Example 14 can include, or can optionally be combined with any one of Examples 1-13 to include subject matter that can include a medical device configured to be at least partially insertable within a patient. The medical device includes a catheter including a catheter proximal end, a catheter distal end, and a sidewall surrounding and defining a lumen extending through the catheter between the catheter proximal end and the catheter distal end. A guidewire includes a guidewire proximal end and a guidewire distal end. The guidewire is sized and shaped to fit within the lumen of the catheter. A coil is disposed within the sidewall of the catheter, wherein the coil is configured to sense a position of the guidewire with respect to the coil. With the guidewire in a first position spaced from the coil, the coil includes a first inductance, and, with the guidewire in a second position proximate the coil, the coil includes a second inductance different from the first inductance.

In Example 15, the subject matter of Example 14 is optionally configured such that the coil is disposed proximate the catheter distal end to sense the guidewire in proximity to the catheter distal end.

In Example 16, the subject matter of Example 14 or Example 15 is optionally configured such that the coil is disposed within the sidewall around the lumen of the catheter.

In Example 17, the subject matter of any one of Examples 14-16 optionally includes a sensor circuit including the coil and a capacitor.

In Example 18, the subject matter of any one of Examples 14-17 optionally includes a control unit electrically coupled to the coil. The control unit is configured to determine the position of the guidewire with respect to the coil based upon an inductance of the coil.

In Example 19, the subject matter of Example 18 is optionally configured such that the control unit includes an output module configured to indicate the position of the guidewire with respect to the coil.

In Example 20, the subject matter of Example 19 is optionally configured such that the output module includes a light that lights up or an alarm that sounds to indicate the position of the guidewire with respect to the coil.

In Example 21, the subject matter of Example 19 or Example 20 is optionally configured such that the output module includes a display screen to indicate the position of the guidewire with respect to the coil.

Example 22 can include, or can optionally be combined with any one of Examples 1-21 to include subject matter that can include a medical device configured to be at least partially insertable within a patient. The medical device includes a catheter including a catheter proximal end, a catheter distal end, and a sidewall surrounding and defining a lumen extending through the catheter between the catheter proximal end and the catheter distal end. A guidewire includes a guidewire proximal end and a guidewire distal end. The guidewire is sized and shaped to fit within the lumen of the catheter. A coil is disposed proximate the catheter distal end within the sidewall of the catheter. The coil is disposed within the sidewall around the lumen of the catheter, wherein the coil is configured to sense a position of the guidewire with respect to the catheter distal end. With the guidewire in a first position spaced from the catheter distal end, the coil includes a first inductance, and, with the guidewire in a second position proximate the catheter distal end, the coil includes a second inductance different from the first inductance.

DETAILED DESCRIPTION

The present invention relates generally to a medical device configured to detect a component extending from the medical device. More specifically, the present invention relates to a catheter configured to detect when a guidewire is at or extending from a distal end of the catheter. In some examples, the present subject matter detects a guidewire at a distal end of a catheter and provides a visual indication at a proximal end of the catheter that the guidewire is located at the distal end of the catheter. Although the description herein relates to a catheter and guidewire, the present subject matter is not intended to be so limited. As such, it is contemplated herein that the present subject matter can be used with various other medical devices and/or components.

In some examples, the present subject matter uses an inductive sensor to detect a guidewire at a distal end of a catheter. The inductive sensor only detects objects within which a magnetic field can be induced, such as, for instance, metallic objects. The present subject matter, in some examples, can be used to replace other methods of knowing that a guidewire is at a distal end of a catheter like using an x-ray (which can be hazardous to a doctor and/or a patient) or using a guidewire with marker bands matched to a catheter. This present subject matter, in various examples, can be used to detect any metallic guidewire at the distal end of a catheter without using x-ray or depending on depth markers. Depth markers are specific to certain guidewire and catheter combinations. In some examples, this present subject matter can be used on any catheter length and with any guidewire that is metallic. The present subject matter can reduce the need for x-ray during a procedure. Moreover, in some examples, since the sensor is built into the catheter, the present subject matter can be used to detect any metallic guidewire at the end of the catheter, regardless of the length of the guidewire or the length of the catheter.

Referring to FIGS. 1-5, in some examples, a medical device 100 is configured to be at least partially insertable within a patient. In some examples, the medical device 100 can be used to access a location within the patient, for instance, in order to perform a medical procedure or a portion thereof.

In some examples, the medical device 100 includes a first elongate member 110 including a first proximal end 110A, a first distal end 110B, and a sidewall 112 surrounding and defining a lumen 114 extending through the first elongate member 110 between the first proximal end 110A and the first distal end 110B. In some examples, the first elongate member 110 includes a catheter. However, in other examples, the first elongate member 110 can include a device other than a catheter, such as, but not limited to, a sheath, an introducer, a hollow guidewire, a probe, a sensing device, or the like, or a combination thereof. Although shown and described herein as having a single lumen 114, it is contemplated, in other examples, that the first elongate member includes two or more lumens extending through the first elongate member.

In some examples, the medical device 100 includes a second elongate member 120 including a second proximal end 120A and a second distal end 120B. The second elongate member 120, in some examples, is sized and shaped to fit within the lumen 114 of the first elongate member 110. In some examples, the second elongate member 120 includes a guidewire. In other examples, the second elongate member 120 can include a device other than a guidewire, such as, but not limited to, a catheter, a probe, a sensing device, or the like, or a combination thereof.

As discussed herein, a common issue with such an arrangement is not knowing whether the distal tip 120B of the second elongate member 120 is extending from the distal end 110B of the first elongate member 110 when the first elongate member 110 is at least partially inserted within a patient. That is, with the distal end 110B of the first elongate member 110 disposed within the patient, the distal end 110B of the first elongate member 110 cannot be seen (with the naked eye). Therefore, it is difficult to determine whether the second elongate member 120 is extending from the distal end 110B of the first elongate member 110 without the use of imaging technology (x-ray, fluoroscopy, or the like) and/or specifically matched first and second elongate members 110, 120.

The medical device 100, in various examples, addresses this problem by allowing a user to know when the second elongate member 120 is at the distal end 110B of the first elongate member 110. In some examples, the first elongate member 110 includes a coil 130 disposed within the sidewall 112 of the first elongate member 110. In some examples, the coil 130 is configured to create a magnetic field. In some examples, the coil 130 is configured to sense a position of the second elongate member 120 with respect to the coil 130. For instance, in some examples, an inductance L of the coil 130 is different between the second elongate member 120 being disposed proximate the coil 130 and the second elongate member 120 being spaced from the coil 130. In this way, the inductance L of the coil 130 is used to indicate the relative position of the coil 130 and the second elongate member 120. By monitoring the inductance L of the coil 130, the coil 130 can be used to sense the position of the second elongate member 120 with respect to the coil 130. In some examples, with the second elongate member 120 in a first position 120' spaced from the coil 130 (FIG. 4), the coil 130 includes a first inductance L', and, with the second elongate member 120 in a second position 120" proximate the coil 130 (FIG. 5), the coil 130 includes a second inductance L" different from the first inductance L'.

In some examples, the coil 130 is disposed proximate the first distal end 110B of the first elongate member 110 to sense the second elongate member 120 in proximity to the first distal end 110B of the first elongate member 110. In this way, the coil 130 can be used to determine if the second elongate member 120 is positioned proximate the distal end 110B of the first elongate member 110. In further examples, the coil 130 can be used to determine if the second elongate member 120 is extending from the distal end 110B of the first elongate member 110. In some examples, the coil 130 is disposed within the sidewall 112 around the lumen 114 of the first elongate member 110. In this way, the second elongate member 120 passes through the coil 130 as the second elongate member 120 moves through the first elongate member 110 and extends from the distal end 110B of the first elongate member 110. In some examples, the first elongate member 110 can include more than one coil. In this way, the two or more coils can be used to detect a presence of the second elongate member 120 at two or more locations along the first elongate member 110. In some examples, the medical device 100 includes first and second conductors 132A, 132B extending from the coil 130 toward the proximal end 110A of the first elongate member 110 to electrically couple the coil 130 to control electronics (described in greater detail below) at the proximal end 110A of the first elongate member 110.

Figure 7:
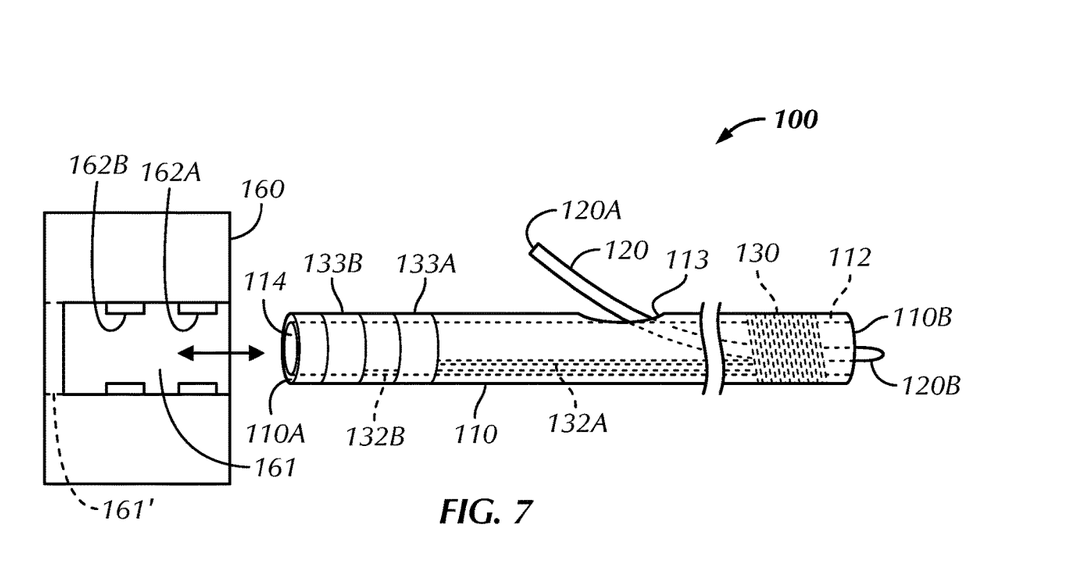
FIG. 7 is a side view of a medical device and a control unit connector in accordance with at least one example of the invention, the medical device and the control unit connector being uncoupled.
Figure 8:
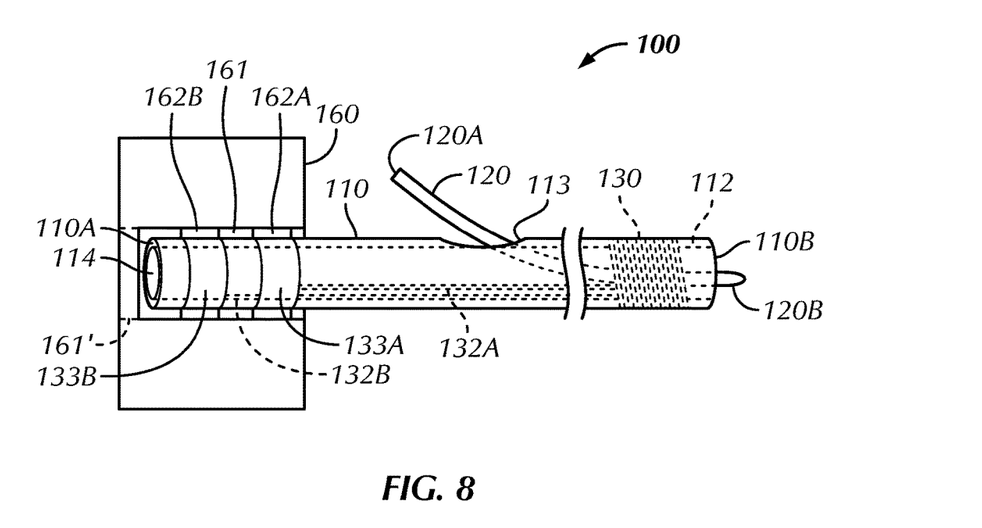
FIG. 8 is a side view of a medical device and a control unit connector in accordance with at least one example of the invention, the medical device being coupled to the control unit connector.

Various configurations are contemplated herein for electrically coupling the coil 130 of the first elongate member 110 to the control electronics. For instance, in some examples, referring now to FIGS. 7 and 8, the first elongate member 110 includes first and second connector electrodes 133A, 133B proximate the proximal end 110A of the first elongate member 110. In some examples, the first and second conductors 132A, 132B extend through the sidewall 112 of the first elongate member 110 from the coil 130 to the first and second connector electrodes 133A, 133B, respectively. In some examples, a receptacle 160 includes a receptacle opening 161 that is configured to accept the proximal end 110A of the first elongate member 110 and electrically couple to the first and second connector electrodes 133A, 133B in order to couple the coil 130 to the control electronics. In some examples, the receptacle 160 includes first and second connectors 162A, 162B configured to correspond and make electrical contact with the first and second connector electrodes 133A, 133B with the proximal end 110A of the first elongate member 110 disposed within the receptacle 160. In some examples, the first and second connectors 162A, 162B are disposed within the receptacle opening 161. In such examples, because, with the proximal end 110A of the first elongate member 110 disposed within the receptacle opening 161 of the receptacle 160 and with the first elongate member 110 coupled to the receptacle 160, the proximal end 110A of the first elongate member 110 and the lumen 114 are inaccessible. To gain access, the first elongate member 110 can include an opening 113 in the sidewall 112 to allow the second elongate member 120 or other devices to be inserted into and/or removed from within the first elongate member 110. That is, the opening 113, in some examples, allows access to the lumen 114 of the first elongate member 110 with the proximal end 110B of the first elongate member 110 coupled to the receptacle 160. In other examples, the receptacle 160 can take a ring-like form (for instance, a cuff or other such device) or another such form that includes a receptacle opening 161' forming a through hole in the receptacle 160 to allow electrical coupling of the first and second connector electrodes 133A, 133B to the first and second connectors 162A, 162B, respectively, while still allowing access to the lumen 114 of the first elongate member 110. Such a configuration allows the second elongate member 120 or other devices to be inserted into and/or removed from within the lumen 114 at the proximal end 110A of first elongate member 110 without the need for the opening 113.

Figure 1:
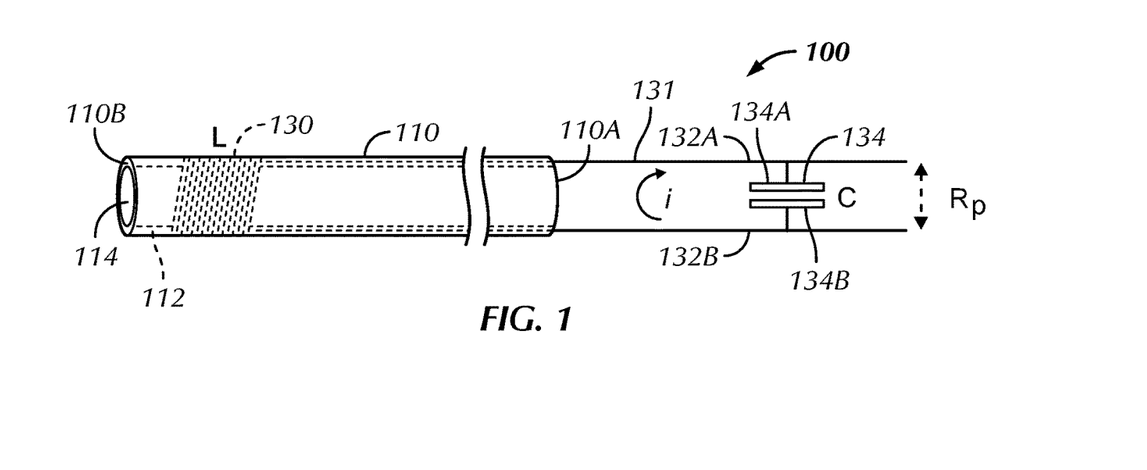
FIG. 1 is a diagrammatic side view of a catheter in accordance with at least one example of the invention.
Figure 2:
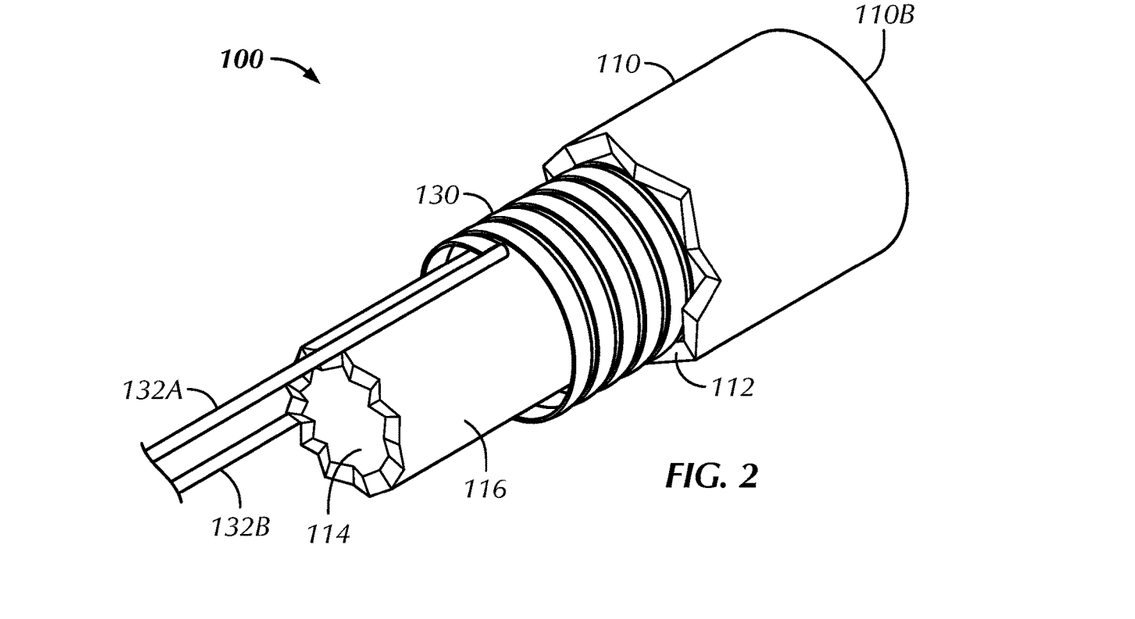
FIG. 2 is an enlarged cut-away view of a distal end of a catheter in accordance with at least one example of the invention.
Figure 3:
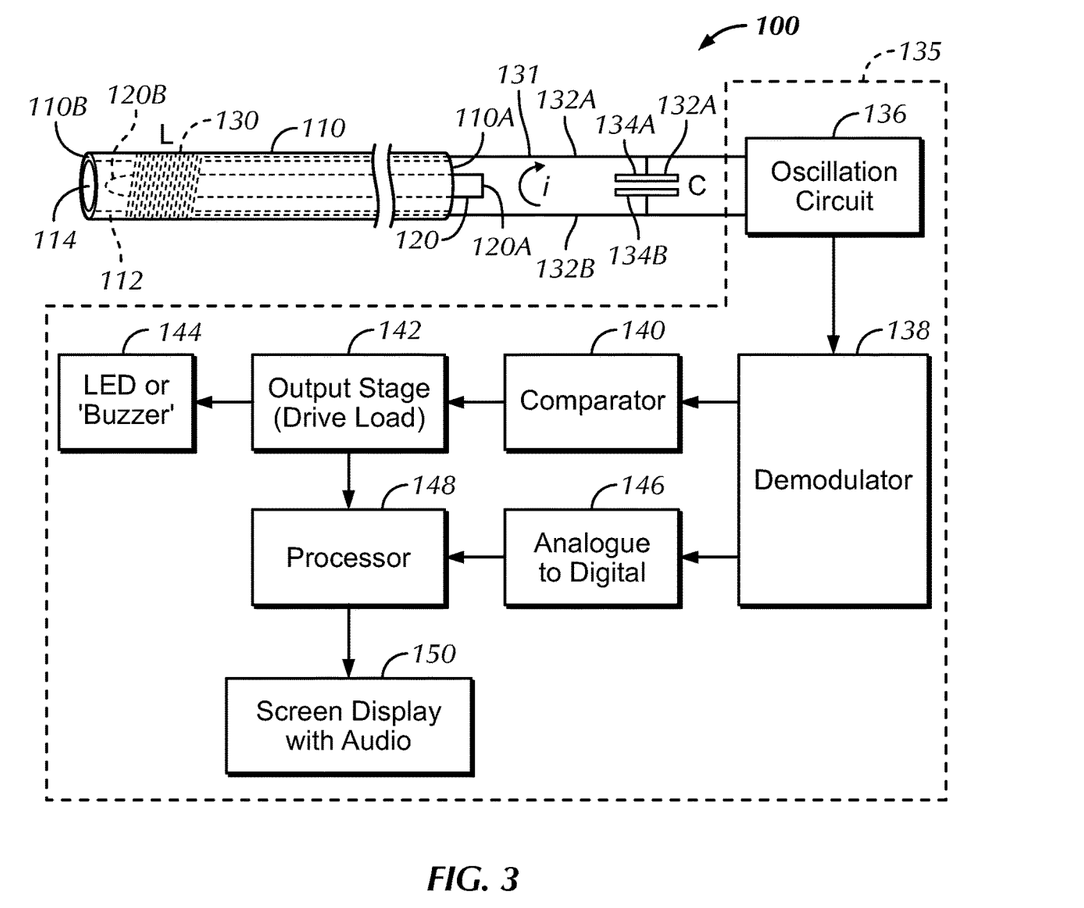
FIG. 3 is a diagrammatic view of a medical device in accordance with at least one example of the invention.

Referring now to FIGS. 1-3, various manufacturing processes can be used to incorporate the coil 130 within the sidewall 112 of the first elongate member 110. In some examples, the first elongate member 110 can be manufactured using a polymer solution casting process utilizing either a mandrel or an inner diameter mold that is immersed in a tank of polymer solution or liquid plastic. The polymer solution forms a thin film liner 116 (FIG. 2) around the mold or mandrel. In some examples, the liner 116 can be used to enhance performance of the first elongate member 110 (for instance, allow for increased lubricity within the lumen 114, allow the first elongate member to withstand greater pressure, or the like). The mold can then be extracted from the tank followed by a curing or drying process. Once the first layer of thin film is adequately solidified, the coil 130 and the first and second conductors 132A, 132B can be added. Additionally, at this stage, in some examples, other components can be added, such as, but not limited to, braided wire, one or more laser-cut hypotubes, and/or engineered metal reinforcements to inhibit kinking or otherwise enhance performance of the first elongate member 110. In some examples, one or more imaging targets can be added depending upon the intended medical application for the first elongate member 110. One or more casting steps can then be performed to encapsulate the coil 130, the first and second conductors 132A, 132B, and any other components such as reinforcements; build up a thickness of the sidewall 112; add one or more additional lumens; and/or optimize column strength of the first elongate member 110. In some examples, one or more cross sections of the first elongate member 110 can be tapered. For instance, the distal end 110B of the first elongate member 110 can be tapered to reduce the moment of inertia and improve flexibility. In some examples, a coating (such as a hydrophilic coating or a hydrophobic coating, for instance) can be deposited on or within the first elongate member 110.

In various examples, the sidewall 112 of the first elongate member 110 can be formed from one or more various materials, including, but not limited to, polytetrafluoroethylene (PTFE); high-density polyethylene (HDPE); a thermoplastic (with or without a filler), such as, but not limited to, polyether block amide, nylon, and/or urethane; polyimide; PTFE-doped polyimide; thermoplastic fluoropolymers, such as, but not limited to, ethylene tetrafluoroethylene (ETFE), fluorinated ethylene propylene (FEP), or the like; and/or silicone. In some examples, the first elongate member 110 can include one or more fillers. In further examples, a filler can be blended into the one or more polymers of the first elongate member 110 to provide radiopacity. Such fillers can include one or more of barium sulfate, bismuth subcarbonate, tungsten, and/or the like.

In some examples, the medical device includes a sensor circuit 131 including the coil 130 and a capacitor 134. In some examples, the capacitor 134 is disposed external to the first elongate member 110; however, this is not intended to be limiting. That is, in other examples, it is contemplated that the capacitor 134 can be included within the first elongate member 110. In some examples, the sensor circuit 131 works on the principle of electromagnetic coupling between the coil 130 (or two or more coils) positioned in the first elongate member 110 and the second elongate member 120 (such as, a metal guidewire or other medical device with a ferromagnetic component).

In some examples, the sensor circuit 131, including the capacitor 134 in parallel with the coil 130, forms a tank circuit. In a tank circuit, in some examples, charge flows back and forth between plates 134A, 134B of the capacitor 134 and through the coil 130. If not replenished from an external circuit, in some examples, the energy oscillates back and forth between the capacitor 134 and the coil 130 until internal resistance makes the oscillations die out. In order to inhibit the oscillations from dying out, in some examples, an oscillation circuit 136 can be used to apply an alternating current i to the sensor circuit 131, thereby driving continuous oscillations. In some examples, this is achieved using a closed-loop op-amp configuration where the tank circuit is connected to a non-inverting input head of an op-amp. Once power is applied, resonance develops in the tank circuit. Essentially, in some examples, the op-amp samples the signal from the tank circuit, amplifies the signal, presents the amplified signal at the op-amp output, and feeds a fraction of the amplified signal back into the tank circuit so that oscillations are maintained indefinitely. In some examples, a frequency of the applied current i is made to match a natural resonant frequency $f_r$ of the sensor circuit 131 so that resonance occurs:

$$f_r = (2\pi)^{-1}((LC)^{-1} - (R_s/L)^2)^{1/2}$$

where $f_r$ is the resonant frequency of the circuit, L is the inductance of the coil 130, C is a capacitance of the capacitor 134, and $R_s$ is an effective impedance across the coil 130.

In some examples, when the second elongate member 120 enters an electromagnetic field induced by the coil 130 in the first elongate member 110, some of the electromagnetic energy is transferred into the second elongate member 120 (for instance, a metal guidewire). In some examples, the transferred energy causes a circulating electrical current called an eddy current in the second elongate member 120. The eddy current flowing in the second elongate member 120, in some examples, induces a reverse electromagnetic field on the coil 130. In some examples, the placement of the second elongate member 120 at or near the coil 130 changes a core permeability of the second elongate member 120, which changes the inductance L of the coil 130 according to the solenoid inductance equation:

$$L = (\mu N^2 A)/l$$

where $\mu$ is the magnetic constant of the coil 130, N is the number of turns of the coil 130, l a length of the coil 130, and A is a cross-sectional area of the coil 130. In some examples, an effective impedance $R_p$ across the sensor circuit 131 is then:

$$R_p = L/R_s C$$

so that when the inductance L of the coil 130 changes, the effective impedance $R_p$ of the sensor circuit 131 also changes.

The proximity of the second elongate member 120 to the coil 130 can be measured in various ways. For instance, in some examples, a voltage across the effective impedance $R_p$ can be measured. In some examples, this voltage changes as the second elongate member 120 gets closer to the coil 130. In other examples, as the second elongate member 120 moves closer to the coil 130, an opposing magnetic field between the second elongate member 120 and the coil 130 requires an increased drive current into the sensor circuit 131, which can be measured and used to indicate a position of the second elongate member 120 with respect to the coil 130.

Referring now to FIGS. 3-6, in some examples, a control unit 135 is electrically coupled to the coil 130. In some examples, the control unit 135 is configured to determine a position of the second elongate member 120 with respect to the coil 130 based upon the inductance L of the coil 130. In some examples, the control unit 135 includes a power cable and plug and is powered using electrical power from a wall socket. In other examples, the control unit 135 includes a battery for power. The control unit 135, in various examples, can include different configurations to determine and indicate to the user the position of the second elongate member 120 with respect to the coil 130, all of which are contemplated herein. The configurations of the control unit 135 described herein are merely exemplary and are not intended to be limiting.

Figure 4:
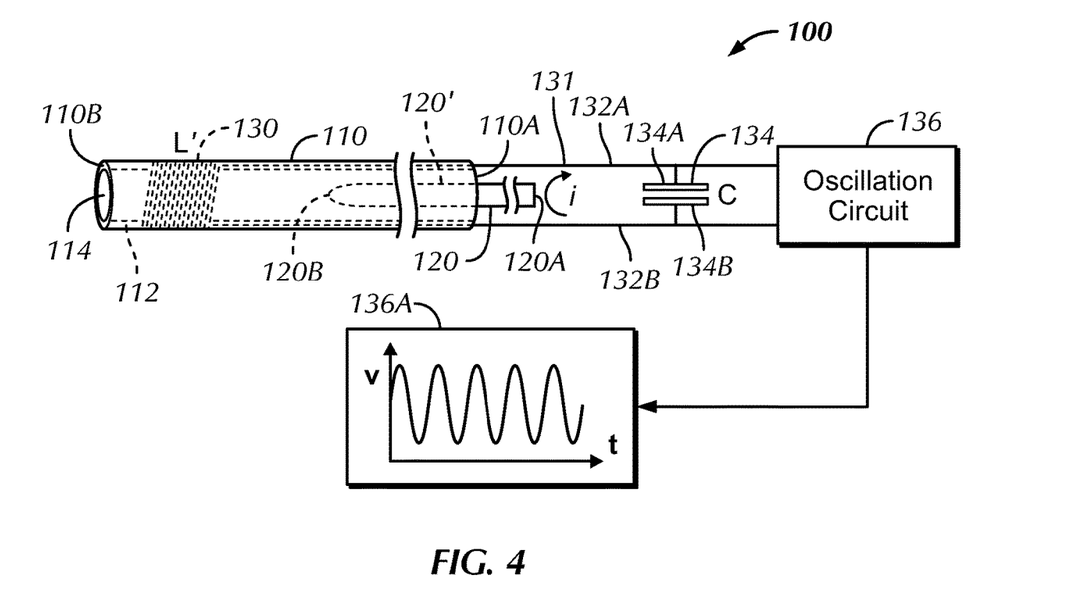
FIG. 4 is a diagrammatic view of a catheter in accordance with at least one example of the invention.
Figure 5:
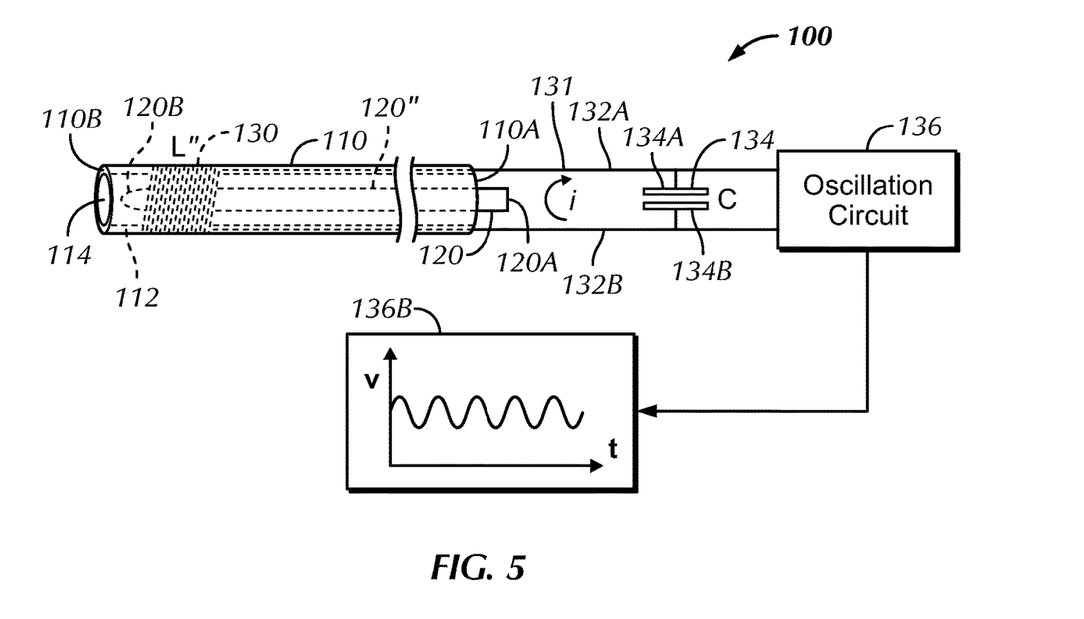
FIG. 5 is a diagrammatic view of a medical device in accordance with at least one example of the invention, the medical device including a guidewire positioned proximate a distal end of the catheter.

In some examples, the control unit 135 includes the oscillation circuit 136, which is configured to produce an output voltage resulting from the oscillation circuit 136 applying the current i to the sensor circuit 131. In some examples, with the second elongate member 120 in the first position 120' spaced from the coil 130, the oscillation circuit 136 produces a first output voltage 136A (FIG. 4). In some examples, with the second elongate member 120 in the second position 120" proximate the coil 130, the oscillation circuit 136 produces a second output voltage 136B (FIG. 5). In some examples, an amplitude of the output voltage varies with proximity of the second elongate member 120 to the coil 130 due to the change in the inductance L of the coil 130. In some examples, an amplitude of the first output voltage 136A (with the second elongate member 120 spaced from the coil 130) is greater than an amplitude of the second output voltage 136B (with the second elongate member 120 proximate the coil 130).

Figure 6:
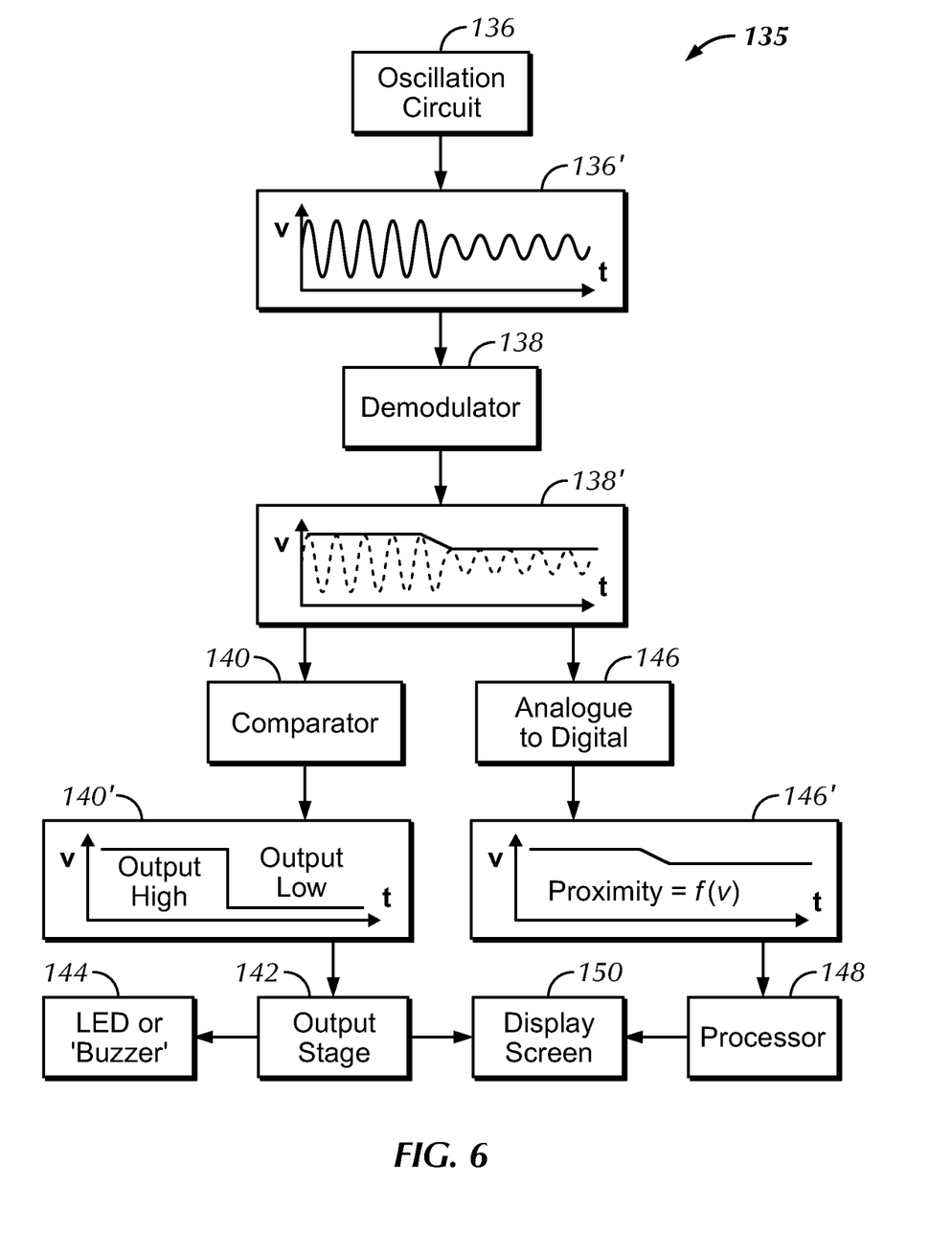
FIG. 6 is a diagrammatic view of a control unit of a medical device in accordance with at least one example of the invention.

Referring specifically to FIGS. 3 and 6, in some examples, the control unit 135 includes a demodulator 138 that is configured to demodulate an output 136' of the oscillation circuit 136 to produce an output 138' that includes an envelope of the alternating current peaks of the output 136' from the oscillation circuit 136. In some examples, the output 136' is demodulated by the demodulator 138 using a filtered rectifier, which converts an AC signal (the output 136') into a DC voltage level (the output 138').

In some examples, the output 138' of the demodulator 138 is fed to a comparator 140, which is configured to give a "High/Low" (or a "No/Yes") output 140' indicating whether the second elongate member 120 is proximate the coil 130. In some examples, the output 140' is then sent to an output stage or module 142 configured to indicate the position of the second elongate member 120 with respect to the coil 130. For instance, in some examples, the output stage 142 is configured to determine, based upon the output 140', whether the second elongate member 120 is spaced from the coil 130 in the first position 120' or proximate the coil 130 in the second position 120".

In some examples, an indicator 144 is powered to notify the user that the second elongate member 120 is proximate the coil 130 (or, conversely, that the second elongate member 120 is spaced from the coil 130). In some examples, the indicator 144 of the output module 142 includes a light that lights up. In further examples, the user can be notified that the second elongate member 120 is proximate the coil 130 (or, conversely, that the second elongate member 120 is spaced from the coil 130) by lighting or actuating a light emitting diode (LED) or other visual indicator. In other examples, either in addition to or instead of a visual indicator, the indicator 144 of the output module 142 includes an alarm that sounds to indicate the position of the second elongate member 120 with respect to the coil 130. In further examples, the user can be notified that the second elongate member 120 is proximate the coil 130 (or, conversely, that the second elongate member 120 is spaced from the coil 130) by the indicator 144 including a speaker to play an alarm, buzz, or otherwise make noise. In instances in which the coil 130 is disposed proximate the distal end 110B of the first elongate member 110, such a notification from the indicator 144 would inform the user that the second elongate member 120 is at or extending from the distal end 110B of the first elongate member 110. Alternatively, in other examples, the indicator 144 can be actuated when the second elongate member 120 is spaced from the coil 130 to indicate to the user that the second elongate member 120 is not extending from the distal end 110B of the first elongate member 110.

In some examples, either in addition to or instead of the output 138' of the demodulator 138 being fed to the comparator 140, the output 138' can be fed to an analogue-to-digital converter 146 to convert the output 138' to a digital output 146', which can then be fed to a processor 148 configured to convert the digital output 146' to a proximity level. From this proximity level, the processor 148, in some examples, can determine whether the second elongate member 120 is proximate (or spaced from) the coil 130 and display such information to the user. In some examples, the processor 148 includes a display screen 150 or other such output device to indicate the position of the second elongate member 120 with respect to the coil 130. In some examples, the display screen 150 can include audio capabilities in order to play an alarm to indicate the position of the second elongate member 120 with respect to the coil 130, either in addition to or instead of graphically depicting such information to the user. In other examples, the output module 142 can be directly connected to the display screen 150 instead of or in addition to being coupled to the processor 148.

In use, in some examples, the sensor circuit 131 works off the inductive sensor principle. The coil 130 at the distal end 110B of the first elongate member 110 generates an oscillating magnetic field. When a metallic component (such as, but not limited to, the second elongate member 120) is introduced into the magnetic field generated by the coil 130, the oscillation of the field is damped. This damping can be detected. Once the damping is detected, the indicator 144 of the control unit 135 lights up, sounds, and/or otherwise indicates that the second elongate member 120 is at the distal end 110B of the first elongate member 110. The indicator 144 stays illuminated, continues to sound, and/or otherwise indicates that the second elongate member 120 is at the distal end 110B of the first elongate member 110 as long as there is a disruption in the magnetic field. When the user wants to position the second elongate member 120 at the distal end 110B of the first elongate member 110 again, the user retracts the second elongate member 120 until the indicator 144 no longer illuminates, sounds, or otherwise indicates that the second elongate member 120 is at the distal end 110B of the first elongate member 110 and then advances the second elongate member 120 until the indicator 144 illuminates, sounds, or otherwise actuates again.

The present inventors have recognized various advantages of the subject matter described herein. The present inventors have recognized, among other things, that the present subject matter can be used to detect a guidewire at or extending from a distal end of a catheter without exposing a patient to unnecessary radiation and without the need for a marker band on a guidewire. Also, the present subject matter is advantageous in that it allows one to know if a guidewire is extending from a distal end of a catheter without the need for specifically matched guidewires and catheters. In various examples, the present subject matter is advantageous in that it provides a way to detect a position of the guidewire with respect to the catheter regardless of guidewire length or catheter length. While various advantages of the example systems are listed herein, this list is not considered to be complete, as further advantages may become apparent from the description and figures presented herein.

Although the subject matter of the present patent application has been described with reference to various examples, workers skilled in the art will recognize that changes can be made in form and detail without departing from the scope of the subject matter recited in the below claims.

The above Detailed Description includes references to the accompanying drawings, which form a part of the Detailed Description. The drawings show, by way of illustration, specific examples in which the present apparatuses and methods can be practiced. These embodiments are also referred to herein as "examples."

The above Detailed Description is intended to be illustrative, and not restrictive. For example, the above-described examples (or one or more elements thereof) can be used in combination with each other. Other embodiments can be used, such as by one of ordinary skill in the art upon reviewing the above description. Also, various features or elements can be grouped together to streamline the disclosure. This should not be interpreted as intending that an unclaimed disclosed feature is essential to any claim. Rather, inventive subject matter can lie in less than all features of a particular disclosed embodiment. Thus, the following claims are hereby incorporated into the Detailed Description, with each claim standing on its own as a separate embodiment. The scope of the invention should be determined with reference to the appended claims, along with the full scope of equivalents to which such claims are entitled.

In this document, the terms "a" or "an" are used to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "about" and "approximately" or similar are used to refer to an amount that is nearly, almost, or in the vicinity of being equal to a stated amount.

In the appended claims, the terms "including" and "in which" are used as the plain-English equivalents of the respective terms "comprising" and "wherein." Also, in the following claims, the terms "including" and "comprising" are open-ended, that is, an apparatus or method that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The Abstract is provided to allow the reader to quickly ascertain the nature of the technical disclosure. It is submitted with the understanding that it will not be used to interpret or limit the scope or meaning of the claims.

The invention claimed is:

1. A medical device configured to be at least partially insertable within a patient, the medical device comprising:
   a first elongate member including a first proximal end, a first distal end, and a sidewall surrounding and defining a lumen extending through the first elongate member between the first proximal end and the first distal end;
   a second elongate member including a second proximal end and a second distal end, the second elongate member being sized and shaped to fit within the lumen of the first elongate member; and
   a sensor circuit including:
     a coil disposed within the sidewall of the first elongate member; and
     a capacitor in parallel with the coil, wherein the sensor circuit is configured to sense a position of the second elongate member with respect to the coil, wherein a current is applied to the sensor circuit with a frequency of the current being selected to match a natural resonant frequency of the sensor circuit so that resonance occurs in the sensor circuit with the current being applied to the sensor circuit.

2. The medical device of claim 1, wherein the coil is disposed proximate the first distal end of the first elongate member to sense the second elongate member in proximity to the first distal end of the first elongate member.

3. The medical device of claim 1, wherein the coil is disposed within the sidewall around the lumen of the first elongate member.

4. The medical device of claim 1, wherein, with the second elongate member in a first position spaced from the coil, the coil includes a first inductance, and, with the second elongate member in a second position proximate the coil, the coil includes a second inductance different from the first inductance.

5. The medical device of claim 4, comprising a control unit electrically coupled to the coil, the control unit configured to determine the position of the second elongate member with respect to the coil based upon an inductance of the coil.

6. The medical device of claim 5, wherein the control unit includes an output module configured to indicate the position of the second elongate member with respect to the coil.

7. The medical device of claim 6, wherein the output module includes a light that lights up or an alarm that sounds to indicate the position of the second elongate member with respect to the coil.

8. The medical device of claim 6, wherein the output module includes a display screen to indicate the position of the second elongate member with respect to the coil.

9. The medical device of claim 5, comprising a receptacle configured to accept the proximal end of the first elongate member and electrically couple the coil to the control unit.

10. The medical device of claim 9, wherein the first elongate member includes an opening in the sidewall to allow access to the lumen of the first elongate member with the proximal end of the first elongate member disposed within the receptacle.

11. The medical device of claim 5, wherein the control unit includes an oscillation circuit configured to apply the current to the sensor circuit and produce an output voltage resulting from the current applied to the sensor circuit, wherein, with the second elongate member spaced from the coil, the oscillation circuit produces a first output voltage, and, with the second elongate member proximate the coil, the oscillation circuit produces a second output voltage.

12. The medical device of claim 1, wherein the first elongate member includes a catheter.

13. The medical device of claim 1, wherein the second elongate member includes a guidewire.

14. A medical device configured to be at least partially insertable within a patient, the medical device comprising:
   a catheter including a catheter proximal end, a catheter distal end, and a sidewall surrounding and defining a lumen extending through the catheter between the catheter proximal end and the catheter distal end;
   a guidewire including a guidewire proximal end and a guidewire distal end, the guidewire being sized and shaped to fit within the lumen of the catheter; and
   a sensor circuit including:
     a coil disposed within the sidewall of the catheter; and
     a capacitor in parallel with the coil, wherein the sensor circuit is configured to sense a position of the guidewire with respect to the coil, wherein a current is applied to the sensor circuit with a frequency of the current being selected to match a natural resonant frequency of the sensor circuit so that resonance occurs in the sensor circuit with the current being applied to the sensor circuit, wherein, with the guidewire in a first position spaced from the coil, the coil includes a first inductance, and, with the guidewire in a second position proximate the coil, the coil includes a second inductance different from the first inductance.

15. The medical device of claim 14, wherein the coil is disposed proximate the catheter distal end to sense the guidewire in proximity to the catheter distal end.

16. The medical device of claim 14, wherein the coil is disposed within the sidewall around the lumen of the catheter.

17. The medical device of claim 14, comprising a control unit electrically coupled to the coil, the control unit configured to determine the position of the guidewire with respect to the coil based upon an inductance of the coil.

18. The medical device of claim 17, wherein the control unit includes an output module configured to indicate the position of the guidewire with respect to the coil.

19. The medical device of claim 18, wherein the output module includes a light that lights up or an alarm that sounds to indicate the position of the guidewire with respect to the coil.

20. The medical device of claim 18, wherein the output module includes a display screen to indicate the position of the guidewire with respect to the coil.

21. The medical device of claim 17, wherein the control unit includes an oscillation circuit configured to apply the current to the sensor circuit and produce an output voltage resulting from the current applied to the sensor circuit, wherein, with the guidewire spaced from the coil, the oscillation circuit produces a first output voltage, and, with the guidewire proximate the coil, the oscillation circuit produces a second output voltage.

22. A medical device configured to be at least partially insertable within a patient, the medical device comprising:
a catheter including a catheter proximal end, a catheter distal end, and a sidewall surrounding and defining a lumen extending through the catheter between the catheter proximal end and the catheter distal end;
a guidewire including a guidewire proximal end and a guidewire distal end, the guidewire being sized and shaped to fit within the lumen of the catheter; and
a sensor circuit including:
a coil disposed proximate the catheter distal end within the sidewall of the catheter, the coil disposed within the sidewall around the lumen of the catheter; and
a capacitor in parallel with the coil, wherein the sensor circuit is configured to sense a position of the guidewire with respect to the catheter distal end, wherein a current is applied to the sensor circuit with a frequency of the current being selected to match a natural resonant frequency of the sensor circuit so that resonance occurs in the sensor circuit with the current being applied to the sensor circuit, wherein, with the guidewire in a first position spaced from the catheter distal end, the coil includes a first inductance, and, with the guidewire in a second position proximate the catheter distal end, the coil includes a second inductance different from the first inductance.

* * * * *